United States Patent [19]

Thorbecke et al.

[11] Patent Number: 4,844,895
[45] Date of Patent: * Jul. 4, 1989

[54] COMPOSITION CONTAINING A PEPTIDE FRAGMENT OF PLATELET FACTOR FOUR AND METHOD FOR RESTORING SUPPRESSED IMMUNE RESPONSES

[75] Inventors: G. Jeanette Thorbecke, Douglaston; Marjorie B. Zucker, New York, both of N.Y.

[73] Assignee: New York University, New York, N.Y.

[ * ] Notice: The portion of the term of this patent subsequent to Oct. 27, 2004 has been disclaimed.

[21] Appl. No.: 79,623

[22] Filed: Jul. 30, 1987

Related U.S. Application Data

[63] Continuation-in-part of Ser. No. 794,105, Nov. 1, 1985, Pat. No. 4,702,908, and Ser. No. 240,407, Aug. 30, 1988, which is a continuation of Ser. No. 72,797, Jul. 13, 1987, abandoned.

[51] Int. Cl.$^4$ .................. A61K 35/14; C07K 7/08
[52] U.S. Cl. .................................. 424/88; 514/8; 514/14; 514/21; 530/327; 530/380; 424/85.1
[58] Field of Search ............... 424/88; 530/327, 380; 514/14, 8, 21

[56] References Cited

U.S. PATENT DOCUMENTS

| | | | |
|---|---|---|---|
| 4,350,687 | 9/1982 | Lipton et al. | 530/322 X |
| 4,399,124 | 8/1983 | Fauve | 514/14 |
| 4,410,511 | 10/1983 | de Wied et al. | 514/13 |
| 4,474,765 | 10/1984 | de Castigione et al. | 514/14 |
| 4,479,896 | 10/1984 | Antoniades | 530/380 |
| 4,517,290 | 5/1985 | Iwasa et al. | 530/325 X |
| 4,683,221 | 7/1987 | Weigle et al. | 514/14 |
| 4,702,908 | 10/1987 | Thorbecke et al. | 530/380 X |

OTHER PUBLICATIONS

Blood, 53:47–62 (1979), Rucinski et al.
Biochim. Biophys Acta, 839: 161–173 (1985), Capitanio et al.
J. Natl. Canc. Inst. 72, 125–132 (1984), Katz et al.
Biochem. Biophys. Res. Comm. 107, 130–135 (1982), Osterman et al.
J. Immunol 134. 3199–3203 (1985), Katz et al.
Cellular Immunol. 100, 57–65 (1986), Katz et al.
Proc-Natl. Acad. Sci. U.S.A. 83, 3491–3495 (1986), Katz et al.

*Primary Examiner*—Howard E. Schain
*Attorney, Agent, or Firm*—Darby & Darby

[57] ABSTRACT

Compositions and methods for modulating immune responses in mammals comprising immunomodulating-effective amounts of PF4 or a biologically active peptide fragment of platelet factor 4 are disclosed herein. Immunomodulation includes one or more aspects of restoration of suppressed immune responses, inhibition of immune suppression (due to exposure of a mammal of an agent that causes suppressor cell activation) and augmentation of normal immune responses.

31 Claims, 3 Drawing Sheets

COMPOSITION CONTAINING A PEPTIDE FRAGMENT OF PLATELET FACTOR FOUR AND METHOD FOR RESTORING SUPPRESSED IMMUNE RESPONSES

This application is a continuation-in-part of copending application Ser. No. 794,105, filed Nov. 1, 1985 of Thorbecke et al, now U.S. Pat. No. 4,702,908 and of a patent application of Thorbecke et al filed Aug. 30, 1988, Ser. No. 240,407 which is a continuation of an application filed July 13, 1987 entitled Composition Containing Platelet Factor Four and Method for Restoring Suppressed Immune Responses Serial No. 072,797, now abandoned. The entire disclosures of said applications are incorporated herein by reference.

This invention relates to compositions and methods of avoiding immune suppression, restoring suppressed immune responses, and augmenting normal immune responses. More particularly, this invention relates to a biologically active peptide fragment of platelet factor 4 (PF4) and to methods using such compositions to modulate immune responses in mammals.

BACKGROUND OF THE INVENTION

Platelet alpha-granules were previously known to contain at least three proteins, which are absent from plasma and are secreted upon clotting: (a) platelet factor 4 (PF4), which binds heparin; (b) another protein that can be cleaved into the so-called low-affinity platelet factor 4 (LA-PF4), which has a weaker ability to bind heparin; and (c) platelet-derived growth factor (PDGF).

The role and properties of PF4 were understood only to a limited extent because PF4 has a short half-life in serum and is not present in an uncomplexed state in any significant amounts. It was known that, upon secretion from platelets, PF4 is combined with chondroitin sulfate (although the factor is thought to have even greater affinity for heparin). The factor was also known to combine with heparan sulfate on the luminal surface of endothelial cells. Other known PF4 properties are its ability to inhibit collagenase activity and to enhance serum elastase activity, and its chemotactic activity for human leukocytes and especially fibroblasts.

Osterman et al (*Biochem. Biophys. Res. Comm.* 107:130–135, 1982) disclosed that a carboxy-terminal tridecapeptide was a potent chemotactic agent (inducing the directed movement of cells in response to a chemical gradient) for monocytes. The synthetic 13 amino acid residue peptide thus comprised the chemotactic active site of PF4 for monocytes.

No immunomodulatory or immunoregulating function had ever been ascribed to any peptide fragments of PF4.

In addition to antibodies, serum and ascites fluid contain a number of factors that can affect immune responses. These factors, which include products of lymphocytes, macrophages and other cells of the hemopoietic system, modulate the immune responses of an organism in a negative or a positive fashion.

Inability or diminished ability to mount immune responses is often present in mammals. It can be the direct result of a pathological condition (such as viral infection, lymphoma, and carcinoma), the treatment of such a condition (such as chemotherapy which is used to treat cancer), or the natural consequence of the aging process.

Immunosuppressed individuals are vulnerable to infection and often succumb to a secondary infection rather than the primary pathological condition from which they suffer. It is, therefore, desirable to devise methods for avoiding or overcoming immune suppression.

To study suppressed immune responses, researchers have established experimental systems in which a state of immune suppression is induced. For example, Katz, I. et al (*J. Nat'l. Canc. Inst.* 72:125, 1984) describe a system where mice are injected intravenously (i.v.) with gamma-irradiated syngeneic lymphoma cells (gamma-RCS) together with sheep erythrocytes (SRBC). Such mice exhibit a markedly suppressed plaque-forming cell (PFC) response. Katz, et al., supra attributed this suppression to a strong proliferation of suppressor T-cells.

The present inventors have previously found that administration of normal mouse and human serum completely reversed immuneresponse suppression in mice injected with gamma-RCS and SRBC.

They further found that T-lymphocytes bound the immunorestorative activity because both spleen cells, (a source rich in mature T-lymphocytes), and cloned cytotoxic T-lymphocytes absorbed the activity from serum. Neither spleen cells from nude mice (T-deficient) nor thymus cells (deficient in mature T-lymphocytes) were cable of absorbing the immunorestorative activity.

The present inventors have identified platelet alpha-granules as the source of the immunorestorative activity and platelet factor 4 as the molecule responsible for such activity. The activity was absent in plasma, or in serum prepared in the absence of platelets, or in serum prepared from a patient lacking platelet alpha-granules. By contrast, an activity with very similar immunorestorative properties was released by isolated human or mouse platelets, after they were stimulated with thrombin.

The present inventors have established that the immunomodulating factor was in fact PF4 (hereinafter alternatively referred to as the holoprotein) by showing the following:

1. The active substance was an alpha-granule constituent (it is absent in serum from alpha-granule-deficient patients) with affinity for heparin.
2. Other known alpha-granule constituents, LA-PF4 and PDGF, had no significant immunomodulating activity.
3. Antiserum to PF4 neutralized the immunomodulating affinity in normal human serum.
4. Isolated PF4 had as much immunomodulating activity as serum or platelet releasate when used in amounts comparable to those believed to be contained in these fluids.

This has been disclosed in the following publications: Katz, I.R. et al *J. Immunol.* 134:3199–3203 1985, Katz, I.R. et al *Cellular Immunol.* 100:57–65 1986, Katz, I.R. et al *Proc. Natl. Acad. Sci.* U.S.A. 83:3491–3455 1986, all incorporated herein by reference.

In light of the above, it would be desirable to obtain fragments of the PF4 molecule capable of expressing the biologic activities of the holoprotein. Such fragments can be economically and easily obtained using conventional solid phase synthesis technique well-known in the art.

OBJECTS OF THE INVENTION

This invention has as its objects to:

increase the understanding of the nature and role of biologically active peptide fragments of PF4;

increase the understanding of the immunosuppressed state of mammals;

develop substances and methods for avoiding immune suppression;

develop substances and methods for restoring immune response in immunosuppressed mammals;

develop substances and methods for augmenting immune response in normal mammals challenged with an antigen;

develop substances having immunomodulating activity and methods for modulating immune response.

These and other objects of the present invention will be apparent to those skilled in the art in light of the present description, accompanying claims, and appended drawings.

BRIEF DESCRIPTION OF THE DRAWING

FIG. 3 is a graph depicting the number of plaque-forming mouse spleen cells after injection of immunosuppressive dilutions.

FIG. 4 is a graph depicting the number of plaque-forming mouse spleen cells after injection of immunosuppressive agent, antigen, and various dilutions of human platelet releasate.

SUMMARY OF THE INVENTION

Figure 1:
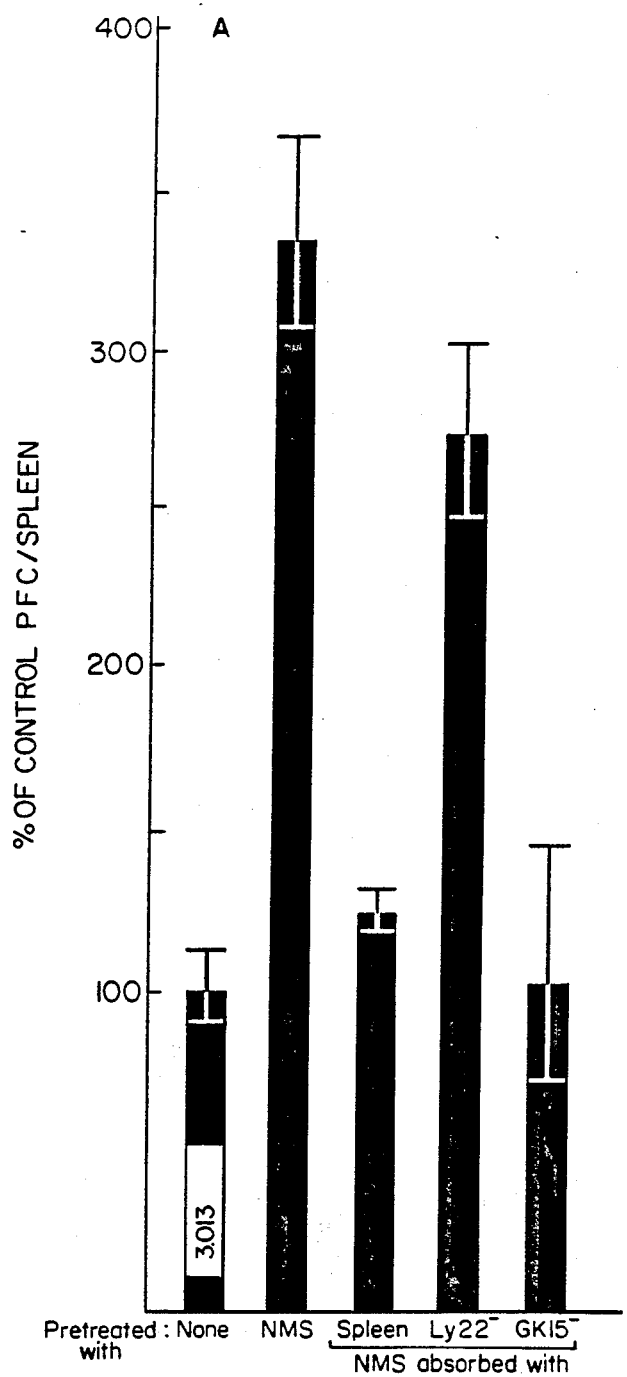
FIGS. 1 and 2 are graphs depicting the number of plaque-forming mouse spleen cells after injection of antigen, immunosuppressive agent and normal mouse serum that had been absorbed with various spleen cell sub-populations.

One aspect of the present invention is directed to a parenteral dosage form for modulating immune response in a mammal comprising as an active ingredient an amount of a biologically active peptide fragment of platelet factor 4 consisting essentially of the amino acid sequence Pro-Leu-Tyr-Lys-Lys-Ile-Ile-Lys-Lys-Leu-Leu-Glu-Ser-COOH effective to modulate immune responses in a mammal. A preferred form of this is a parenteral dosage form containing said peptide fragment and a pharmaceutically acceptable carrier.

Another aspect of the present invention is directed to a method for modulating immune response in a mammal in need of such treatment comprising administering to said mammal an amount of the above-mentioned peptide fragment of platelet factor 4 effective to modulate immune response in said mammal.

As used herein, "immune modulation" includes one or more aspects of restoration of suppressed immune responses, inhibition of immune suppression (due to exposure of or administration to a mammal of an agent that causes suppressor cell activation), and augmentation of normal immune responses.

DETAILED DESCRIPTION OF THE INVENTION

In accordance with the present invention, PF4, biologically-active peptide fragments and preparations containing such material can be used to restore immune responses in immunosuppressed mammals, to inhibit suppression of immune response in mammals treated with immunosuppressing substances, and to augment immune response in normal mammals challenged with an antigen (e.g. vaccinated).

The present inventors previously established that mammalian serum and mammalian platelet releasate contained an immunomodulating substance and that this substance was PF4. This was surprising because not immunomodulating effects had been previously found in a platelet factor.

The present inventors have now unexpectedly discovered that a tridecapeptide (hereinafter alternatively referred to as "the biologically active fragment of PF4"), comprising the 13 amino acids at the carboxyterminal end of platelet factor 4, is biologically active in that it is active in preventing Con A-induced suppression in mice. About three times more of the PF4 tridecapeptide of the present invention, in proportion to moles of the PF4 holoprotein are effective in restoring suppressed immune responses. This increase may be due to the fact that this small peptide (molecular weight approximately 1300 Daltons) is probably rapidly cleared from the bloodstream. This is a most surprising finding in that the tridecapeptide can manifest its biological effects before such clearance.

Platelet releasate can be prepared by exposing platelet suspensions (from whole blood fractionation) to increasing concentrations of thrombin (from about 0.05 U/ml of about 1.0 U/ml). (Higher concentrations of thrombin are not harmful, but they are unnecessary.) The material released from the platelets, termed "platelet releasate", contains all of the immunomodulating activity present in purified PF4. Other substances, such as calcium ionophore (A23187), that also cause platelets to release their alpha-granule contents, can be used instead of thrombin.

PF4 is a substance that is normally released from platelets during clotting. It is present in the serum of normal mammals, including humans (about 5 micrograms/ml) or in platelets (approximately 18 micrograms per $10^9$ platelets).

PF4 may be prepared from platelet releasate and purified by affinity chromatography using heparin-agarose as the absorbent. Preferably, PF4 is purified by the method of Rucinski, et al (*Blood* 53:47, 1979) incorporated by reference.

A tridecapeptide, having the amino acid sequence Pro-Leu-Tyr-Lys-Lys-Ile-Ile-Lys-Lys-Leu-Leu-Glu-Ser-COOH, comprising the carboxy-terminal 13 amino acid residues of human PF4, is preferably synthesized and purified using methods wellknown in the art, for example, the methods of Osterman, D.G. et al, *Biochem. Biophys. Res. Comm.* 107:130–135, 1982, incorporated by reference or those disclosed below in Example 10.

The PF4 tridecapeptide can be produced by other methods, such as by recombinant DNA techniques well-known in the art, or can be obtained by enzymatic or chemical fragmentation of the PF4 holoprotein and recovery of biologically active material. However, the advantage of employing the chemically-synthesized tridecapeptide of the present invention is that it can be produced from pure amino acids. PF4 holoprotein must be purified from biologic material, e.g. human blood and fractions thereof, and could possibly be contaminated by viruses, such as hepatitis or human immunodeficiency virus (HIV). The PF4 holoprotein (or fragments thereof) prepared by recombinant DNA techniques may contain other harmful materials, such as toxins, made by the organism used to synthesize the material, thus limiting their usefullness.

Fresh platelets are washed with pyrogen-free, sterile standard buffers and resuspended to $2 \times 10^9$/ml. PF4 is released by addition of 1U thrombin/ml or of 250 nM A23187, or of 50 uM arachidonic acid (providing the platelet donor has not ingested aspirin). The suspension is incubated for 1 hour and then centrifuged. The supernatant is applied to a 5 ml column of heparin-agarose (Pharmacia or Pierce Chem. Co.) equilibrated with 0.5M NaCl, 0.05 M Tris, pH 8.0. The column is washed with the same buffered NaCl until no more protein is eluted. Next the column is eluted with 1.5 M NaCl, 0.05 M Tris, pH 8.0 causing PF4 to come off in a small volume. It can be diluted (1:10), just prior to injection, in 0.1 to 1% human serum albumin in distilled water to restore to isotonicity. Additional dilutions can be made in buffered, isotonic albumin solutions.

Although any PF4-containing preparation (normal serum, or platelet releasate) can be used to modulate immune response, it is preferable to use purified PF4 preparations in a pharmaceutically acceptable carrier, especially when treating immunosuppressed mammals.

Suitable carriers include but are not limited to buffered, isotonic human serum albumin solutions (for stabilization: Capitanio et al. *Biochem. Biophys. Acta* 839:161–173 1985).

The preferred mode of administration for PF4 or biologically-active fragments thereof is intravenous injection. The amount of PF4 or the biologically active fragment thereof that are effective for a particular therapeutic application varies depending on the extent of immune suppression, the amount and potency of the immuno-suppressing agent whose effects are to be overcome by PF4, the weight of the mammal, and the time of administration.

Preferred PF4 holoprotein amounts for treating humans will be within the broad range of about 500 $\mu$g to about 5 mg per treatment. The broad range for mice is between about 0.18 and about 18 micrograms per treatment. A particularly preferred regimen for the treatment of mice is one intravenous injection of 0.2 ml of platelet releasate ($10^8$ platelets/ml) or 0.2 ml of purified PF4 in saline (at a concentration of 1 to 5 micrograms/ml) given one day before, simultaneously with, or one day after, administration of 5–10 $\mu$g Con A, or another agent which activates suppressor cells.

Preferred amounts of the tridecapeptide of the present invention for treating humans will be within the broad range of about 250 micrograms and 25 milligrams per treatment. The broad range for mice would be within about 0.1 micrograms and about 10 micrograms per treatment. The same treatment regimens, mentioned above when using the PF4 holoprotein, are expected to be effective when using the tridecapeptide fragment except that about 3 times more (on a molar basis) of the fragment of the present invention would be employed.

The above per-treatment dosage limits are broadly defined. The number of treatments necessary will vary according to the condition to be treated and might also vary from mammal to mammal. For example, when PF4 preparations are used as a vaccine adjuvant, one treatment will be necessary soon before or soon after or simultaneously with the vaccination. When used to combat immune suppression one or more additional treatments might be necessary at appropriate intervals if the immune suppression persists or recurs (This can be determined by monitoring the immune response of the treated mammal.) Finally, when used to avoid immune suppression, one treatment will be generally necessary soon before or soon after, or simultaneously with, exposure of the mammal to an agent that induces activation of suppressor cells.

The minimum effective dose of PF4 or the biologically-active fragment thereof can be established by routine experimentation using serially diluted preparations of PF4 or biologically-active fragment thereof.

PF4 and the biologically-active fragment thereof restore immune responses by binding to activated peripheral T-cells of the suppressor phenotype.

The suppression of the immune response in mice by concanavalin A (Con A) is a generally recognized phenomenon and can be shown in all strains of mice tested if the Con A is injected prior to antigen. PF4 was able to overcome the Con A-induced suppression in mice if injected one day after Con A, at the same time as antigen (SRBC), or one to two hours before Con A on the day prior to antigen injection. Furthermore, the PF4 holoprotein, the PF4 tridecapeptide of the present invention, platelet releasate and serum where each able to overcome Con A-induced suppression in a dose-dependent fashion. Injection of releasate from as few as $10^6$ human platelets had a measurable effect and releasate from $2 \times 10^7$ platelets restored the number of plaque-forming cells to the unsuppressed value. Greater amounts of releasate increased the number of antibody forming plaques far above the number produced by injecting the antigen into mice whose antibody formation had not been suppressed by Con A. PF4 can also stimulate antibody formation even in mammals not treated with an immunosuppressive agent.

Therefore, injecting PF4 or the biologically-active peptide fragment of PF4 of the present invention to enhance immune response is an important application of the present invention in man, not only to restore the immune response to patients with immune suppression, but also to serve as an adjuvant to enhance immune response to vaccines and other immunogens. In the latter case, administration of PF4 or the biologically-active fragment of PF4 would preferably take place simultaneously with and/or soon before (such as a day before) immunization.

The present invention is further described below by reference to specific examples, which are intended to illustrate the present invention without limiting its scope.

EXAMPLE 1

Source and Purification of Platelet Releasate, PF4 and the PF4 Tridecapeptide

CB6F1 mice (Charles River Breeding Laboratories, Inc., Wilmington, MA.) were bled from the tail. For preparation of serum, the blood was allowed to clot at room temperature for one to two hours, after which serum was collected and stored at $-70°$ C.

For the preparation of plasma, blood was collected into citrate buffer (0l.1 ml, 0.105 M buffered sodium citrate per 0.9 ml blood), spun for ten minutes at 2000 rpm, and stored at $-70°$ C. To prepare platelets, platelet-rich plasma was prepared from human citrated blood by slow centrifugation, brought to pH 6.5 with citric acid, and centrifuged to pellet the platelets. The platelets were washed in Tyrode's solution which contained 0.01 M HEPES (N-2-hydroxyethylpiperazine-N'-2' ethanesulfonic acid, from Sigma Chemical Co., St. Louis, MO), 0.05% bovine serum albumin, 20 mM sodium citrate, and 0.1 mg per ml apyrase (Sigma), pH 6.5, resuspended in HEPES-buffered Tyrode solution at pH 7.4 without citrate, centrifuged after adding 5 mM EDTA, and resuspended in the same buffer without apyrase or albumin to a concentration of 2 to $5\times10^9$ cells per ml. Thrombin (Upjohn Company, Kalamazoo, MI) was added at the concentration of 1 unit per ml and the samples were gently shaken for two minutes. The samples were incubated for one hour, centrifuged at 1,000 times for five minutes, the supernatants were removed, and stored frozen at $-20°$ C. Mouse platelet releasate was prepared similarly, except that the blood was collected into 0.1 volume of 50 mM EDTA and the platelets were resuspended in 0.01 M HEPES—saline.

Human PF4 was purified from platelet releasate according to the method of Rucinski et al (*Blood* 61:1072-1080, June, 1983), incorporated by reference. Briefly, PF4 from platelet releasate bound to heparin-agarose (Pierce Chemical Co., Rockford, IL) with high affinity and was eluted at 1.2-1.5 M NaCl).

The tridecapeptide PF4 fragment of the present invention was custom-synthesized by a commercial laboratory (Peninsula Labs Inc., Belmont, CA) and was synthesized using the solid phase method essentially as described (Merrifield, R.B., *J. Amer. Chem. Soc.* 86: 304-305 1963 and Steward, J.M. et al, *Solid Phase Peptide Synthesis*, Pierce Chemical Co., 1984, both references incorporated herein by reference) using the resins described below. The C-terminal amino acid residue (serine) was coupled to a chloromethylated copolymer of polystyrene and divinylbenzene. The other twelve amino acid residues, protected with tert-butyloxycarbonyl (t-Boc) at their amino terminus, were added sequentially. The peptide chain was assembled stepwise while it was covalently anchored at one end to the above-mentioned insoluble resin, followed by liberation of the product after completion of the synthesis. The liberated product was purified before use using high performance liquid chromatography (HPLC), well-known in the art.

EXAMPLE 2

Reversal of Con A-Induced Suppression

Concanavalin A (Miles—Yeda Ltd., Research Products, Israel) was reconstituted with saline and kept frozen. Dilutions from the frozen stock were stored at 4° C. and injected i.v. into mice one day prior to antigen, sheep erythrocytes (SRBC). SRBC were obtained from Colorado Serum Company (Denver, Colorado) washed, counted and injected intraperitoneally (i.p.) in mice. Human serum or platelet releasate was administered i.v. one to two hours before Con A i.v.

The spleens of the mice were assayed for plaque-forming cells (PFC) on day 5 after injection of sheep red blood cells. The assay employed was as follows: single-cell suspensions were prepared from individual spleens of mice. The cells were suspended in Hanks' Balanced Salt Solution (Gibco Laboratories, Grand Island, New York) and washed. Direct PFC were enumerated using the well-known method of Jerne, N.K. et al (in *Cell-Bound Antibody*, Amos, E. and Koprowsky, H. eds., Wistar Institute Press. pp. 109-111, 1983) with the slide modification of Mishell, R.I. and Dutton, R.W. (*J. Exp. Med.* 126:423, 1967), both incorporated by reference.

The results are summarized in Table 1 below.

TABLE 1

| Day 0[a] SRBC | Day −1 Human Serum or Plt. Releasate | Con A | Geom. Mean PFC/Spleen (X̄S.E.) | | | |
|---|---|---|---|---|---|---|
| | | | Expt. 1 | Expt. 2 | Expt. 3 | Expt. 4 |
| + | None | — | 99,200 (1.1) | 79,400 (1.2) | 5,600 (1.1) | 8,700 (1.1) |
| + | None | 50 μg | 20,370 (1.1)[d] | — | — | — |
| + | Day −1[c] | 50 μg | 65,300 (1.0)[d] | — | — | — |
| + | None | 5 μg | — | 84,760 (1.2)[f] | 1,540 (1.3) | 4,400 (1.1)[g] |
| + | None | 10 μg | — | 29,660 (1.2)[e] | — | — |
| + | Day −1[b] | 10 μg | — | 63,250 (1.1)[e] | — | — |
| + | Day −1[b] | 5 μg | — | 120,980 (1.1)[f] | 77,600 (1.2) | — |
| + | Day −1[c] | 5 μg | — | — | 44,900 (1.1) | 51,590 (1.1)[g] |
| + | Day 0[b] | 5 μg | — | — | — | 51,500 |

[a] SRBC were injected ip: $1 \times 10^8$ in Expt. 1; $5 \times 10^7$ in Expts. 3 and 4.
[b] 50 μl serum/mouse, i.v., 1-2 hrs before Con A i.v.
[c] 0.1 ml. 1:50 diluted platelet releasate ($10^9$ platelets/ml) injected i.v. 1-2 hrs before Con A i.v.
[d] $p < 0.0001$.
[e] $p < 0.01$.
[f] $p < 0.05$.
[g] $p < 0.0001$.
Results are expressed as geometric mean X̄SE (n = 4) of PFC per spleen assayed 5 days after i.p. injection of SRBC.

(a) SRBC were injected ip: $1\times10^8$ in Expt. 1; $5\times10^7$ in Expts. 3 and 4.
(b) 50 μl serum/mouse, i.v., 1-2 hrs before Con A i.v.
(c) o.1 ml. 1:50 diluted platelet releasate ($10^9$ platelets/ml) injected i.v. 1-2 hrs before Con A i.v.
(d) $p<0.0001$.
(e) $p<0.01$.
(f) $p<0.05$.
(g) $p<0.0001$.

Results are expressed as geometric mean $\bar{x}$ SE (n=4) of PFC per spleen assayed 5 days after i.p. injection of SRBC.

As can be seen in Table 1, the suppression induced by 5-50 micrograms of Con A was at least partially reversible both by serum and by platelet releasate. In addition, the factor frequently caused a much higher response than in unsuppressed control mice. The results in Table 1 (Expt. 4) also show that serum was equally effective at enhancing immune response whether it was injected one day after Con A, or one to two hours before Con A, on the day prior to antigen injection.

EXAMPLE 3

Prevention by PF4 of Con A-Induced Suppressor Cell Formation In Vivo as Assayed On Immune Response In Vitro In order to determine whether Con A-induced suppressor cells were present in spleens of mice treated with both platelet releasate and Con A, the spleen cells from such mice were co-cultured with normal syngeneic spleen cells.

In vitro immunizations were performed according to the method of Mishell and Dutton (*Science* 153:1004, 1966—incorporated by reference), using spleen cells from mice injected i.v. one day earlier with 25 micrograms of Con A (platelet releasate usually preceding Con A by one hour), or with platelet releasate alone. One to $5 \times 10^6$ cells from these mice were added to $5 \times 10^6$ normal spleen cells. Cultures were prepared in 35 mm petri dishes (Falcon, Div. Beckton, Dickinson & Company, Oxnard, CA) and immunized with 50 microliters of 0.5% SRBC in the total volume of 1 ml RPMI-1640 (Gibco, Grand Island, NY) per dish, supplemented with 5% fetal calf serum, 3% Interleukin-1 (prepared as described by Hoffmann, M.K. *J. Immunology* 125:2076, 1980—incorporated by reference), nonessential amino acids, sodium pyrophosphate, glutamine, antibiotics and 2 mercaptoethanol ($5 \times 10^{-5}$ M). The assay for plaque-forming cells was the same as in Example 2 except that in vitro cultures were harvested on day 4. Results from these in vitro cultures are expressed as PFC per culture and percent of control response.

The results are presented in Table 2 below.

TABLE 2

| Pretreatment of Spleen Cell Donor (Day −1) | No. Spleen Cells[a] Added to Culture | Expt. 1 | | Expt. 2 | |
|---|---|---|---|---|---|
| | | PFC/Dish[b] | Control Response (%) | PFC/Dish[b] | Control Response (%) |
| None | $5 \times 10^6$ | 380 | 100 | — | |
| | $2.5 \times 10^6$ | — | | 1,600 | 100 |
| | $1 \times 10^6$ | 970 | 100 | 1,360 | 100 |
| Con A 25 μg(i.v.) | $5 \times 10^6$ | 140 | 37 | — | |
| | $2.5 \times 10^6$ | — | | 730 | 46 |
| | $1 \times 10^6$ | 460 | 47 | 1,100 | 81 |
| Platelet Releasate + Con A 25 μg (i.v.) | $5 \times 10^6$ | 405 | 107 | — | |
| | $2.5 \times 10^6$ | — | | 2,140 | 134 |
| | $1 \times 10^6$ | 1,060 | 109 | 1,500 | 111 |
| Platelet Releasate | $2.5 \times 10^6$ | — | | 2,170 | 136 |
| | $1 \times 10^6$ | — | | 1,360 | 100 |

[a] Added to $5 \times 10^6$ normal spleen cells together with 0.025% SRBC on Day 0.
[b] PFC/dish determined on Day 4.

Table 2 shows that the response of SRBC of the normal spleen cells was indeed suppressed by $1-5 \times 10^6$ spleen cells from mice injected with Con A (25 micrograms) in a dose—dependent fashion. On the other hand, spleen cells from mice injected with platelet releasate alone or in combination with Con A were not suppressive; they slightly enhanced or did not affect the responses of the spleen cells from uninjected mice in vitro. Injection of releasate thus prevented the induction of suppressor cells by Con A.

EXAMPLE 4

Absorption of Immunoregulatory Factor from Serum by Cells from Different Lymphoid Organs Mouse spleen cells can absorb the immunoregulatory factor from human or mouse serum. In order to confirm and expand this finding, 1 ml o serum, diluted 1:2, was absorbed twice for thirty minutes at 4° C. using half the number of cells for each absorption as are listed for spleen (Spl), lymphnode (LN) and thymus (Thy) in Table 3. Each CB6F$_1$ mouse received 0.2 ml of a 1:4 dilution of absorbed or unabsorbed serum i.v. one to two hours before administration of $2 \times 10^6$ SRBC i.v. Plaque-forming cell response was measured as in Example 2.

TABLE 3

| Day 0 SRBC | Day 0* Human Serum | Day −1 Con A | Day 5** Geom. Mean PFC/ Spleen | ($\bar{X}$ S.E.) |
|---|---|---|---|---|
| + | None | − | 8,810 | (1.1)[a] |
| + | Unabsorbed | − | 20,520 | (1.2)[a b] |

TABLE 3-continued

| Day 0 SRBC | Day 0* Human Serum | Day −1 Con A | Day 5** Geom. Mean PFC/ Spleen | ($\bar{X}$ S.E.) |
|---|---|---|---|---|
| + | None | + | 2,930 | (1.1) |
| + | Unabsorbed | + | 14,300 | (1.1)[b c d] |
| + | Absorbed $2 \times 10^8$ Spl | + | 3,100 | (1.1)[c] |
| + | Absorbed $4 \times 10^7$ Spl | + | 6,870 | (1.1) |
| + | Absorbed $4 \times 10^7$ LN | + | 5,570 | (1.1)[d] |
| + | Absorbed $2 \times 10^8$ Thy | + | 13,870 | (1.1) |
| + | Absorbed $4 \times 10^7$ Thy | + | 13,960 | (1.1) |

*One ml (1:2 diluted) serum was absorbed twice for 30 min. at 4° C. using half the number of CB6F$_1$ mouse cells indicated for each absorption. Spl = spleen: LN = lymph node; Thy = thymus.
**n = 4.
[a] p = 0.002;
[b] N.S. (p = .081);
[c] p < 0.0001;
[d] p < 0.0001.

The above results confirm that spleen cells can indeed absorb the platelet factor from human serum. Lymph node cells were approximately as effective as spleen cells in absorbing this factor, while thymus cells did not remove any of the immunomodulatory activity.

High PFC responses were also obtained when serum was injected with SRBC into mice which were not injected with Con A, as shown on line 2 of Table 3. Hence, human serum enhanced the response of SRBC in the absence as well as in the presence of Con A. This experiment shows the potential of platelet releasate for use as an adjuvant in vaccine preparations for administration to non-immunosuppressed patients.

EXAMPLE 5

Properties of T cells With

Affinity For Platelet Factor 4

The inventors investigated the subpopulation of T cells in the spleen which are directly implicated in this activity. In these experiments, the suppression was induced by injection of gamma-RCS cells in SJL mice (Jackson Laboratory, Bar Harbor, ME). Gamma-RCS cells are gamma-irradiated syngeneic lymphoma cells, derived from a primary tumor of an SJL/J mouse and maintained by weekly serial passage i.v. of $10^7$ tumor-infiltrated lymph node cells into syngeneic young mice. Intravenous injection of $2 \times 10^7$ gamma-irradiated RCS cells simultaneously with SRBC was used to suppress a normal anti-SRBC response. Plaque-forming cell response was measured 5 days after injection, as in the Con A-induced suppression.

Spleen cells at $5\times 10^7$ cells per ml were treated with appropriate monoclonal antibodies at 4° C. for 30 minutes. Cells were then spun down and resuspended in a 1:20 diluted rabbit complement to which 10 micrograms of DNAse (Worthington, Freehold, NJ) was added to help remove DNA from killed cells and prevent their clumping. The cells were then incubated at 37° C. for 45 minutes, washed and counted. After elimination of different subpopulations of T cells, the remaining spleen cells were used for incubation with normal sera (4° C. for 45 minutes). The following monoclonal antibodies were used to characterize the phenotype of T cells with affinity for platelet releasate: GK 1.4, anti-L3T4a; 19/178, anti-Lyt2.2; SK 70.94, anti-Ly-m6.IE; T28.45.9, anti-Ly-m22.2; B16-146, anti-Qa4; B16-167, anti-Qa5; 2-2.1, anti-Lyt1.2; and a conventional allo-antibody specific for Qa1. These antibodies were obtained from Dr. U. Hammerling and F.W. Shen (Sloan-Kettering Institute for Cancer Research). Commercially available antibodies anti-L3T4 (TIB 207), anti-Lyt 2.2 (TIB 210), from ATCC (Rockville, MD) could have been used instead.

Alternatively, monoclonal antibodies can be prepared as described below in a representation example of the production of monoclonal antibodies to Qa4 (B16-146) and Qa5 (B16-167) alloantigens (Hammerling, G.J. et al. *J. Exp. Med.* 150:108-146, 1979 —incorporated by reference).

Four female AKR mice (The Jackson Laboratory, Bar Harbor, ME) are immunized i.v. with a mixture of $2\times 10^7$ spleen and thymus cells of male C57BL/6 mice. A booster of $3\times 10^7$ thymocytes and $3\times 10^7$ spleen cells is administered 3 weeks after the initial immunization. Three days after the 2nd immunization, the recipients' spleens are removed using wellknown sterile dissection techniques and single cell suspensions are made by teasing the spleens with a fine forceps. Spleen cells are harvested by centrifugation at 400 $\times$g for 5 min., washed and counted; approximately $10^8$ spleen cells are used for hybridization.

Mouse myeloma cells (e.g. P3$\times$63 Ag8), a commercially available line from American Type Culture Collection (Rockville, MD) can be used as fusion partners. The myeloma cells are maintained in Eagle's minimal essential medium (MEM) containing 15% fetal calf serum (all culture media from GIBCO, Grand Island, NY).

Fusion is carried out by the well-known technique of Galfre and Milstein (*Meth. Enzymol.* 73:1, 1981 incorporated by reference). $10^7$ myeloma cells and $10^8$ mouse spleen cells are mixed in serum-free media and centrifuged at 400 $\times$g for 5 min. The cell pellet is resuspended in 0.5-1 ml of warm fusion medium containing 50% w/v PEG preparation (10g liquid warm polyethylene glycol MW 1500; 10 ml Dulbecco's modified Eagle's Medium (DMEM) pH 7.6 —PEG is from J.T. Baker Chemical Co., Philadelphia, PA), stirred, mixed with DMEM, centrifuged, resuspended and distributed at a density of $5\times 10^5$ cells per well into 96-well microplates (Costar, Cambridge, MA).

After overnight incubation, the cells are exposed to HAT selective medium (Flow Laboratories, Inc., McLean, VA). Cultures are incubated at 37° C. in an atmosphere of 95% air and 5% $CO_2$ and grown in HAT medium for 10-15 days.

The growing hybrids are propagated by i.p. injection of hybridomas in appropriate Swiss nude mice in order to obtain high-titered ascitic fluid. Immunoglobulin classes or subclasses of monoclonal antibodies are determined by immunodiffusion according to the method of Ouchterlony and Nilsson, (*Handbook of Experimental Immunology*, D.M. Weir (ed) Chapter 19. Blackwell, Oxford. 1978, incorporated by reference) using monospecific rabbit antimouse immunoglobulin sera, commercially available from Litton Bionetics (Kensington, MD). In many cases, purification of the monoclonal antibodies is not necessary. If desired, however, monoclonal antibodies can be purified from hybrid culture supernatants (or ascites fluid) by precipitation with ammonium sulfate or by ion exchange chromatography, as is well known in the art.

The results of the assay described above are presented in FIG. 1. The results shown graphically in FIG. 1, describe a splenic PFC response 5 days after simultaneous i.v. injection of $10^7$ SRBC and $2\times 10^7$ gamma-RCS in SJL mice. Some groups of mice were also injected i.v. with (a) 0.05 ml of unabsorbed normal mouse serum (NMS); (b) serum absorbed (2x, as in Example 4) with whole spleen cell suspension; or (c) with spleen cell suspension from which different subpopulations of cells were eliminated by treatment with monoclonal antibodies and complement (indicated as negative for the subpopulation which was killed). The response of mice injected with $10^7$ SRBC without gamma-RCS was taken as the control High responses were noted when the spleen cell suspension left after treatment with monoclonal antibody and complement was unable to absorb the augmenting factor from serum.

Figure 2:
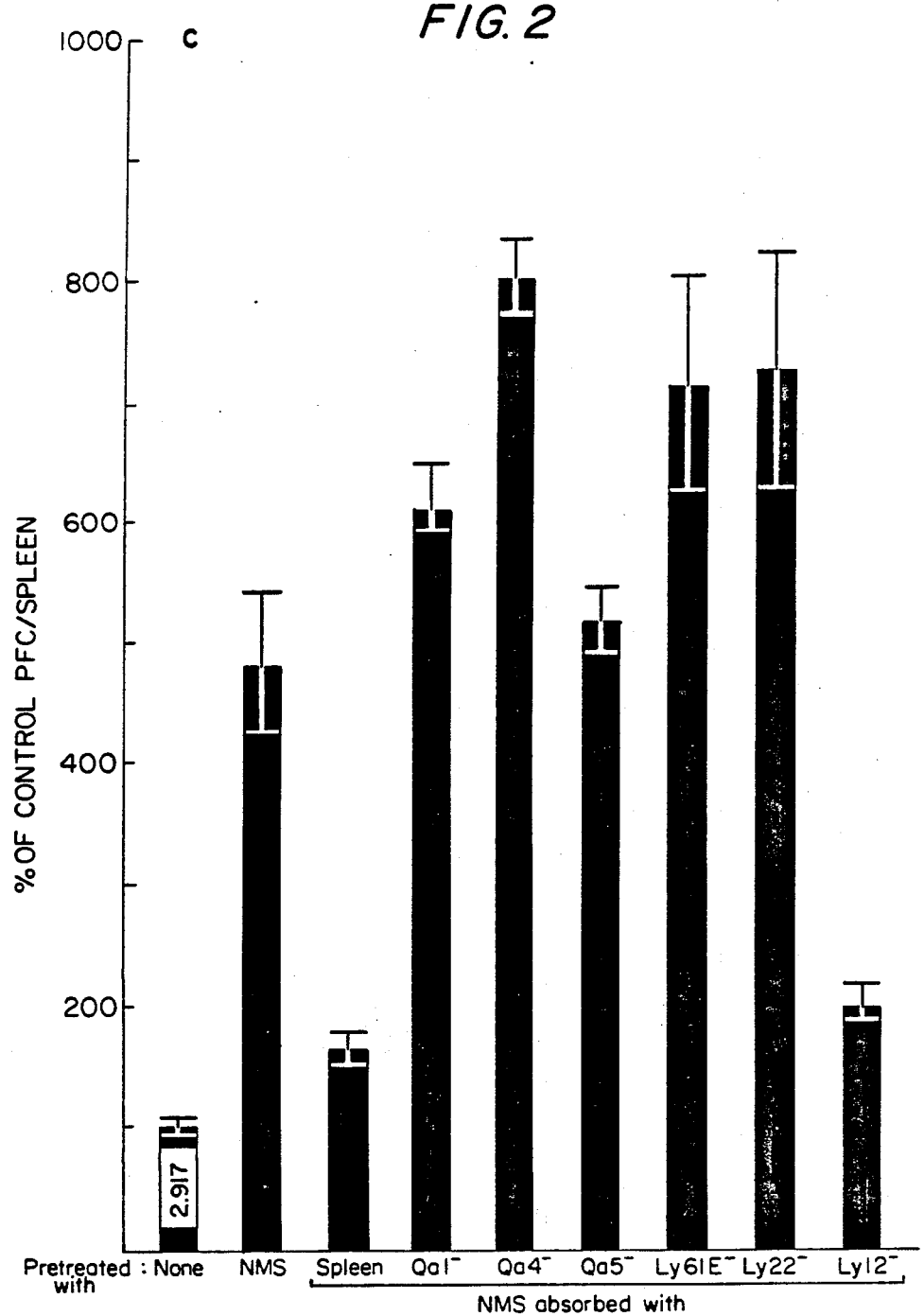

FIGS. 1 and 2 show that the activity of the platelet factor was absorbed by spleen cells from which the L3T4+ or Ly1+2− cells had been removed. However, when serum absorption was performed with spleen cells lacking Ly2+, or Ly22+ cells, immunomodulatory activity remained equal to that of unabsorbed of the serum with spleen cells from which the Qa1+, the Qa4+ and the Qa5+ or the Ly6.IE+ cells had been removed by cytotoxic antibody and complement treatment.

From the data presented in FIGS. 1 and 2, the phenotype of the T cells capable of absorbing the factor from serum appears characteristic of activated suppressor T cells. The phenotype is Ly2+, L3T4−, Ly1−, Ly22+, Qa1+, Qa4+, Qa4+, and Ly6.IE+. Since the platelet factor reversed suppression as effectively when injected together with antigen one day after Con A (see the data presented above), as when injected one hour prior to Con A (as shown in Table 1), it clearly can counteract suppressor cells that have already been activated.

EXAMPLE 6

Dose-Response Curve of Immunoregulatory Activity

Human serum or human platelet releasate was diluted and injected into mice in order to determine the minimum amount of these materials needed to overcome induced suppression. Although undiluted serum had the largest effect, dilutions as high as 1:10 increased the number of plaque-forming cells above the control value, as seen in FIG. 3. In this experiment, suppression was induced by the injection of gamma-RCS as shown in Example 5. Releasate from a human platelet suspension produced similar results, as shown in FIG. 4. The greatest effect was noted after injection of material which had been diluted 1:60 or 1:180 or the equivalent of as few as $10^6$ platelets. Releasate from ⅓ of this amount was still slightly active. The higher concentrations of serum and releasate increased the number of PFC above the number obtained in unsuppressed mice injected with antigen alone.

EXAMPLE 7

Reversal of Immunoregulatory Activity in Human Serum by Goat Antiserum to PF4

In order to prove that PF4 was responsible for the immunoregulatory activity in human serum or releasate, the ability of goat antiserum to PF4 to neutralize this activity was tested. Goat antiserum to human PF4 was produced using conventional techniques, but could have been obtained as part of a kit for radio immunoassay of PF4 from Abbott Laboratories (Chicago, IL). Thus, 0.05 ml of human serum was mixed with 0.008 ml of goat anti-human PF4 or 0.008 ml of normal goat serum and incubated for 20 minutes at 4° C. prior to injection. Immunosuppression was induced using 5 μg Con A as in Example 2.

The results are presented below in Table 4.

TABLE 4

| Mice Injected With SRBC and | | |
|---|---|---|
| 5 μg Con A | Additional Material | Geom. Mean PFC/Spleen* on Day 5 |
| − | None | 8,720 |
| + | None | 4,380 |
| + | Human Serum | 51,590 |
| + | Human Serum + goat anti-PF4 | 13,190 |
| + | Human Serum + N1 goat serum | 49,470 |
| + | Goat anti-PF4 | 10,000 |

*S.E. (antilog) ≤ 1.1; n = 4.

Goat serum containing antibody to PF4 nearly abolished the immunomodulatory activity of normal human serum while normal goat serum had no effect when used in a similar amount. Goat anti-PF4 antiserum injected alone also had no significant effect in reversing immunosuppression in mice.

EXAMPLE 8

IMmunomodulatory Activity of Platelet Alpha-Granule Constituents

When treated with thrombin or A23187 (Calcium ionophore), platelets also release alpha granule constituents other than PF4. In particular, they release LA-PF4 and PDGF. The inventors tested the ability of LA-PF4 and PDGF to overcome suppression induced by 5 μg Con A.

The results are presented below in Table 5.

TABLE 5

| Mice Injected With SRBC and | | Geom. Mean of PFC/Spleen* On Day 5 | | |
|---|---|---|---|---|
| 5 μg Con A | Additional Material | Expt. 1 | Expt. 2 | Expt. 3 |
| − | None | 16,090 | 12,450 | 32,590 |
| + | None | 8,000 | 4,880 | 12,920 |
| + | Releasate | 14,190 | 29,920 | 30,740 |
| + | PF4 | ND | 22,910 | 34,420 |
| + | LA-PF4 | ND | 9,440 | ND |
| + | PDGF | 8,370 | ND | ND |
| + | PF4 + heparin | ND | ND | 27,280 |

*Geometric mean. Antilog of standard error ≤ 1.1; n = 4

At concentrations well below those present in serum, PDGF (0.003 μg per mouse) had little or not activity, LA-PF4 (0.6 μg per mouse) a small amount, and purified PF4 (0.2 to 0.6 μg per mouse), had very marked activity.

A mixture containing 0.1 units per ml heparin and 14 ug per ml PF4 was also tested for its immunoregulatory activity. This mixture was diluted 1:15 and 0.2 ml was injected per mouse. This amount of PF4, when mixed with the amount of heparin was unable to neutralize additional heparin in the heparin-neutralization assay. Thus, all of the PF4 was presumably bound to heparin. Nevertheless, the PF4 was still able to reverse immunosuppression (line 7, Table 5). This suggests that the heparin-combining property of PF4 has little influence on its ability to interact with the appropriate T-cells.

EXAMPLE 9

Inhibition of Immunomodulatory Activity From Human Platelets

Platelet releasates had little immunomodulatory activity if human platelets were stimulated in the presence of a protease inhibitor. In experiment 1, Table 6, the suppressive agent was $2 \times 10^7$ gamma-RCS cells injected i.v. into SJL mice together with $10^7$ SRBC on day 0. In experiments 2-5, Table 6, 5 ug of Con A was injected into CB6F$_1$ mice on day -1, followed by SRBC, at $2 \times 10^7$ i.p. or $2 \times 10^6$ i.v., injected on day 0. Platelet releasate was produced by shaking samples with 250 nM of the ionophore A23187 (Calbiochem-Behring, San Diego, CA). Platelet releasate was diluted to represent about $10^8$ platelets per ml before i.v injection of 0.2 ml per mouse on day -1 (prior to Con A) or on day 0 (prior to antigen).

The serine protease inhibitor (p-amidinophenyl)methanesulfonyl fluoride, APMSF (California Medicinal Chemistry Corp., San Francisco, CA) was added at a concentration of 100 micromolar to the platelet suspension either before or after the ionophore A23187. The supernatant was dialyzed against a large volume of Tyrode's solution after incubation at 37° C.

The results are presented below in Table 6.

TABLE 6

INHIBITION BY APMSF OR BY BOILING OF THE GENERATION OF IMMUNOREGULATORY ACTIVITY FROM HUMAN PLATELETS STIMULATED WITH 250 nM A23187

| Mice Injected With SRBC and | | Geom. Mean PFC/Spleen | | | | |
|---|---|---|---|---|---|---|
| Suppressive Agent | Platelet Releasate | Expt. 1 | Expt. 2 | Expt. 3 | Expt. 4 | Expt. 5 |
| − | − | 17,450 | 5,585 | 16,090 | 12,445 | 22,760 |
| + | − | 8,270 | 1,540 | 8,000 | 4,875 | 7,540 |
| + | + | 20,990 | 44,870 | 14,185 | 29,920 | 24,570 |
| + | APMSF Added Before Releasate | 8,900 | 8,709 | 6,240 | 3,940 | 6,630 |
| + | APMSF Added After Releasate | ND | ND | 13,850 | ND | 25,120 |
| + | Boiled Before Incubation | 9,550 | ND | 7,690 | ND | 8,785 |

TABLE 6-continued
INHIBITION BY APMSF OR BY BOILING OF THE GENERATION OF IMMUNOREGULATORY ACTIVITY FROM HUMAN PLATELETS STIMULATED WITH 250 nM A23187

| Mice Injected With SRBC and | | Geom. Mean PFC/Spleen | | | | |
|---|---|---|---|---|---|---|
| Suppressive Agent | Platelet Releasate | Expt. 1 | Expt. 2 | Expt. 3 | Expt. 4 | Expt. 5 |
| + | Boiled After Incubation | ND | 28,820 | 12,940 | ND | 24,220 |

As stated above, releasates had little immunoregulatory activity if human platelets were stimulated in the presence of APMSF. In contrast, full activity was noted if APMSF was added after the samples had been incubated for 60 minutes (Table 6). Results obtained with boiled samples similarly suggested that enzyme activity was necessary for generation of immunomodulatory activity. Little activity was found in samples that were centrifuged 2 minutes after the addition of A23187, and boiled promptly, whereas activity was only slightly decreased by boiling samples that had first been incubated for sixty minutes (Table 6). Platelets secreted all of their activity within 2 minutes; activity was the same in unboiled samples that were centrifuged two minutes after addition of A23187 and then incubated without the platelet pellet as it was in samples that were incubated for 60 minutes after addition of A23187 and then centrifuged to remove the pellets. The protease inhibitor itself would not have been responsible for the inhibition of the immunomodulatory activity because any inhibitor that escaped hydrolysis was removed by dialysis. Furthermore, samples in which APMSF was added after incubation of the A23187stimulated platelets were fully active.

The purified PF4 used in experiments in Table 5 (Example 8) was made from releasates that had been incubated prior to boiling; hence, any enzymatic changes produced in this material had probably already taken place.

The results may be interpreted as due to an inhibition of an activatory of PF4 activity by for example, a protease, or to destruction of an inhibitor of antibody synthesis which masks the effects of PF4.

Example 10

Immunoregulatory Activity of a PF4 Tridecapeptide

A tridecapeptide fragment, consisting essentially of the carboxy-terminal 13 amino acid residues of human PF4 and having the amino acid sequence Pro-Leu-Tyr-Lys-Lys-Ile-Ile-Lys-Lys-Leu-Leu-Glu-Ser-COOh was dissolved in 0.1% crude human serum albumin (which was free of the PF4 holoprotein) in isotonic saline and assayed for immunoregulatory activity, e.g. the reversal of Con A-induced immune suppression.

Mice were injected with 10 micrograms of Con A i.v. on day $-1$ (except in the positive control, which received no Con A) and on day 0 with $2.5 \times 10^6$ SRBC per mouse as in Example 2 above. On day $-1$, the mice also received either: Nothing (100% control), Con A only, platelet releasate (equivalent to the amount of PF4 holoprotein contained in the platelet releasate from $2 \times 10^7$ platelets or about 0.12 microgram/mouse) and various concentrations of the above-mentioned synthetic C-terminal peptide of human PF4. The results are presented in Table 7 below.

TABLE 7
IMMUNOREGULATORY ACTIVITY OF SYNTHETIC C-TERMINAL TRIDECAPEPTIDE OF PF4

| Material Injected* On Day $-1$ | Geom. Mean PFC/Spleen ($\bar{X}SE$) (n)* | | | | | |
|---|---|---|---|---|---|---|
| | Expt.1 | | Expt.2 | | Expt.3 | |
| | PFC | % | PFC | % | PFC | % |
| None (100% Control) | 11,100(1.2) | 100 | 20,500(1.2) | 100 | 14,400 | 100 |
| None (Con A only) | 3,500(1.2) | 32 | 7,200(1.5) | 35 | 4,900(1.3) | 34 |
| Platelet Releasate | 9,300(1.1)[a] | 84 | 29,700(1.1)[a] | 145 | 15,300(1.3) | 106 |
| 2.5–7 μg Tridecapeptide | 10,900(1.2)b | 99 | | | 38,800(1,1)[b] | 270 |
| 0.7–1 μg Tridecapeptide | 10,400(1.1)[b] | 95 | 46,300x(1.1)[b] | 226 | | |
| 0.07μg Triedecapeptide | 4,000(1.4) | 37 | | | | |
| 0.007 μg Triedecapeptide | 5,700(1.4) | 52 | | | | |

*n for each point is equal to 5–10 mice
[a]Significantly different from values for mice injected with Con A only (p ≦ 0.05).
[b]Significantly different from values for mice injected with Con A only (In Expt.1: p = 0.0005 and 0.013, respectively; in Expt. 2 p = 0.03; and in Expt. 3 p ≦ 0.0001.

As demonstrated in Table 7, the tridecapeptide was active in reversing the immunosuppression induced by Con A when 0.7–7 micrograms was administered to mice. Since this peptide is substantially smaller than PF4 (i.e. 13 amino residues out of 70 for the intact protein), on a molar basis its activity is less than that of the holoprotein.

Example 11

Absorption of the PF4 Tridecapeptide Fragment by Cells from Different Lymphoid Organs In order to demonstrate that the PF4 peptide fragment of the present invention had the same biologic activity as the PF4 holoprotein, the ability of spleen or thymus cells to absorb the PF4 tridecapeptide was examined. The experiments were performed exactly as described for the PF4 holoprotein in Example 4 above, except that 0.5 (Expt. 1) or 2.5 micrograms (Expt. 2) of the PF4 tridecapeptide was administered. The results are presented in Table 8.

TABLE 8

Absorption of Immunoregulatory Activity of C-Terminal Tridecapeptide of PF4 by Cells from Mouse Spleen and Thymus

| Material injected | Geom mean PFC/Spleen (X̄ S.E.) | | | |
|---|---|---|---|---|
| | Expt. 1 | | Expt. 2 | |
| | Geom. Mean | S.E. | Geom. Mean | S.E. |
| SRBC | 8,164 | (1.24) | 14,930 | (1.25) |
| SRBC + Con A | 2,846 | (1.04) | 5,633 | (1.16) |
| SRBC + Con A + Tridecapeptide | 23,488 (0.5 μg/mouse) | (1.07) | 38,790 (2.5 μg/mouse) | (1.13) |
| SRBC + Con A + peptide absorbed with normal spleen cells | 8,426 | (1.14)[a] | 10,315 | (1.60)[c] |
| SRBC + Con A + peptide absorbed with normal thymus cells | 19,305 | (1.31)[b] | | |
| SRBC + Con A + peptide absorbed with spleen cells from athymic mice | | | 22,419 | (1.20) |

[a] $P = 0.001$ vs unabsorbed peptide
[b] $P = 0.626$ vs unabsorbed peptide; $P = 0.058$ vs peptide absorbed with normal spleen cells
[c] $P = 0.39$ vs Con A alone The above results show that spleen cells can absorb the biologically active tridecapeptide PF4 fragment in a manner similar to that of the PF4 holoprotein. Neither thymus cells from normal mice nor spleen cells from athymic mice were capable of absorbing the immunoregulatory activity.

The higher PFC responses, obtained in Example 4 above using the PF4 holoprotein (when human serum was injected with SRBC in the absence of Con A) would also be expected to be induced by the biologically active human PF4 tridecapeptide fragment of the present invention. The results show the use of PF4 or the biologically active tridecapeptide PF4 fragment of the present invention as an adjuvant in vaccine preparations for administration to non-immunosuppressed patients.

The invention has been described above by reference to preferred embodiments. It is understood, however, that many additions, deletions and modifications will be apparent to one of ordinary skill in the art in light of the present description without departing from the scope of the invention, as claimed below.

What is claimed is:

1. A method for modulating immune response in a mammal in need of such treatment comprising administering to said mammal a composition comprising an effective amount for modulating said immune response of a biologically active peptide fragment of platelet factor 4 comprising the amino acid sequence Pro-Leu-Tyr-Lys-Lys-Ile-Ile-Lys-Lys-Leu-Leu-Glu-Ser-COOH.

2. The method of claim 1, comprising administering to said mammal an amount of said peptide fragment of platelet factor 4 sufficient to improve or restore immune response in a mammal immunosuppressed through activation of T-suppressor cells.

3. The method of claim 1, comprising administering to said mammal an amount of said peptide fragment of platelet factor 4 sufficient to improve or restore immune response in a mammal immunosuppressed by exposure of said mammal to an agent or antigen which induces T-suppressor cells.

4. The method of claim 1, comprising administering to said mammal an amount of said peptide fragment of platelet factor 4 sufficient to enhance the immune response of a normal mammal, said response resulting from the administration of an antigenic agent to said mammal.

5. The method of claim 1 wherein said amount ranges between about 0.1 micrograms and about 10 micrograms of said peptide fragment of platelet factor 4 per treatment for mice.

6. The method of claim 1 wherein said amount ranges between about 250 micrograms and about 25 milligrams of said peptide fragment of platelet factor 4 per treatment for man.

7. The method of claim 1 wherein said peptide fragment is administered intravenously.

8. The method of claim 3 comprising administering said peptide fragment to said mammal prior to exposure of said mammal to said agent.

9. The method of claim 3 comprising administering said peptide fragment to said mammal substantially simultaneously with administration of said agent.

10. The method of claim 3 comprising administering said peptide fragment to said mammal after administration of said agent.

11. The method of claim 4 comprising administering said peptide fragment to said mammal prior to administration of said agent.

12. The method of claim 4 comprising administering said peptide fragment to said mammal substantially simultaneously with administration of said agent.

13. The method of claim 4 comprising administering said peptide fragment to said mammal after administration of said agent.

14. The method of claim 1 further comprising monitoring the immune response of said mammal.

15. A parenteral dosage form for modulating the immune response in a human comprising an effective amount for modulating immune response of a biologically-active peptide fragment of platelet factor 4 comprising the amino acid sequence Pro-Leu-Tyr-Lys-Lys-Ile-Ile-Lys-Lys-Leu-Leu-Glu-Ser-COOH and a pharmaceutically acceptable carrier or diluent.

16. The dosage form of claim 15 wherein said effective amount ranges between about 250 micrograms and 25 milligrams of said peptide fragment.

17. The dosage form of claim 15, wherein said amount is effective for restoring the immune response suppressed by activation in said human of peripheral T-cells of the suppressor phenotype.

18. The dosage form of claim 15, wherein said amount is effective for preventing immune response suppression caused by exposure of said mammal to an agent or antigen which induces suppressor T-cells.

19. The dosage form of claim 15, wherein said amount is effective for augmenting the immune response of said human to an antigenic agent.

20. The dosage form of claim 15, wherein said carrier is physiological buffered saline solution containing human serum albumin for stabilization.

21. A parenteral dosage form for augmenting the immune response of a mammal to an antigen by suppression of the activation of suppressor T-cells in said mammal which accompanies exposure of the immune system of a mammal to said antigen, said dosage form comprising an amount of said antigen sufficient for immunization of said mammal and an amount of a biologically active peptide fragment of platelet factor 4 comprising the amino acid sequence Pro-Leu-Tyr-Lys-Lys-Ile-Ile- Lys-Lys-Leu-Leu-Glu-Ser-COOH effective for augmenting said response.

22. The dosage form of claim 21, wherein said effective amount is within the range between about 0.1 micrograms and about 25 milligrams.

23. The dosage form of claim 21, said dosage form comprising a vaccine.

24. The dosage form of claim 18, said dosage form comprising a vaccine adjuvant.

25. The dosage form of claim 15 in the form suitable for intravenous administration.

26. The dosage form of claim 21 in a form suitable for intravenous administration.

27. The dosage form of claim 21, said carrier being physiological buffered saline solution containing serum albumin for stabilization.

28. A pharmaceutical dosage form for administration to a human comprising an effective amount for enhancing the immune response of said human of a biologically active peptide comprising the amino acid sequence Pro-Leu-Tyr-Lys-Lys-Ile-Ile-Lys-Lys-Leu-Leu-Glu-Ser-COOH and a pharmaceutically acceptable carrier.

29. A pharmaceutical dosage form comprising an effective amount of enhancing the immune response in a mammal in need of such treatment of a biologically active product consisting of a peptide having the amino acid sequence Pro-Leu-Tyr-Lys-Lys-Ile-Ile-Lys-Lys-Leu-Leu-Glu-Ser-COOH and a pharmaceutically acceptable carrier.

30. The pharmaceutical dosage form of claim 29 further comprising a mammalian antigen.

31. A vaccine against a mammalian antigen comprising an effective amount for stimulating the immune response of said mammal of a biologically active peptide consisting of the amino acid sequence Pro-Leu-Tyr-Lys-Lys-Ile-Ile-Lys-Lys-Leu-Leu-Glu-Ser-COOH, said mammalian antigen, and a pharmaceutically acceptable carrier.

* * * * *